United States Patent
Chen et al.

(10) Patent No.: US 7,338,806 B2
(45) Date of Patent: Mar. 4, 2008

(54) REAGENT KIT OF GLOBAL ANALYSIS FOR PROTEIN EXPRESSION AND METHOD FOR QUALITATIVE AND QUANTITATIVE PROTEOMIC ANALYSIS USING THE SAME

(75) Inventors: Shu Hui Chen, Tainan (TW); Jue Liang Hsu, Tainan County (TW); Sheng Yu Huang, Taipei County (TW)

(73) Assignee: National Cheng Kung University, Tainan (TW)

( * ) Notice: Subject to any disclaimer, the term of this patent is extended or adjusted under 35 U.S.C. 154(b) by 443 days.

(21) Appl. No.: 10/909,294

(22) Filed: Aug. 3, 2004

(65) Prior Publication Data

US 2005/0064515 A1    Mar. 24, 2005

(30) Foreign Application Priority Data

Sep. 23, 2003    (TW) .............................. 92126189 A

(51) Int. Cl.
*G01N 23/00*    (2006.01)

(52) U.S. Cl. ........................................................ 436/57
(58) Field of Classification Search ..................... None
See application file for complete search history.

(56) References Cited

OTHER PUBLICATIONS

Dottavio-Martin et al. Analytical Biochemistry 1978;87:562-565.*
Gluck et al. Biochimica et Biophysica Acta 1990;1038:146-151.*

* cited by examiner

*Primary Examiner*—Ralph Gitomer
*Assistant Examiner*—Bin Shen
(74) *Attorney, Agent, or Firm*—Bacon & Thomas PLLC

(57) ABSTRACT

The present invention provides a reagent kit of global analysis for protein expression and method for qualitative and quantitative proteomic analysis using the same, characterized in which isotope labeling reagent is utilized to modify enzymatically cleaved peptides in normal or perturbed cells and subsequently tandem mass spectrometry is used to identify protein sequence, and at the same time, accurately measure the protein expression level based on variation in signal intensity.

1 Claim, 5 Drawing Sheets

REAGENT KIT OF GLOBAL ANALYSIS FOR PROTEIN EXPRESSION AND METHOD FOR QUALITATIVE AND QUANTITATIVE PROTEOMIC ANALYSIS USING THE SAME

BACKGROUND OF THE INVENTION

1. Field of the Invention

The present invention discloses a reagent kit of global analysis for protein expression and method for qualitative and quantitative proteomic analysis using the same, which combines stable isotope labeling and tandem mass spectrometry to accurately quantify protein expression.

2. Description of Related Art

Protein over-expression is often associated with the presence of disease or the administration of drug. Protein regulation is not only related to the transcribed or translated message, but also the post-translational modification. Currently there are three general approaches to the measurement of protein expression in cells: (1) observing the expression of mRNA by microarray to determine whether the post-transcriptional protein is over-expressed. But this method is based on the premises that mRNA expression is positively correlated with protein expression. However in real biological systems, such positive correlation is rarely present. Thus this method cannot cover all types of protein expression and its reproducibility or accuracy is questionable; (2) carrying out quantitative analysis by using two-dimensional electrophoresis and staining gel separated proteins with coomassie blue stain, silver stain, or immunoblotting. This method is limited by the inherent limitations of the two-dimensional electrophoresis, which shows poor sensitivity and reproducibility in the case of extremely acidic or basic proteins, very large or small proteins, protein expressed at very low level, or membrane proteins; (3) using mass spectrometry in conjunction with chemical reagent (commonly isotope labeling reagent). This method is direct, accurate and reproducible. The commercialized isotope-coded affinity tags (ICAT) reagent is an example.

The technique of culturing cells with isotope which allows isotope to be expressed in proteins through metabolism and thereby observing the protein expression of cells in different environments is widely known. But this method concerns the rate of isotope substitution in cells and is unsuitable for in vivo experiment. The technology of modifying proteins with isotope labeling reagent and then using mass spectrometry for quantitative analysis was conceived in the past five years. As mass spectrometry improves in sensitivity and resolution, it provides a powerful analytical tool as we enter the era of proteomics from genomics. The most noticeable example is the development of ICAT reagent. ICAT comprises an affinity end (e.g. biotin affinity end), which aids in sample purification and binds with the protein reaction group (PRG) through a linker. The linker may be isotopically coded, commonly with hydrogen ($^1H$) and deuterium ($^2D$). This technology based on the different isotopic molecules with the similar chromatographic properties and different mass spectrum is excellent. But the applications of LC/MS are still limited. For examples: (1) the large structure of labeling reagent oftentimes poses difficulty to the fragmentation process in tandem mass spectrometry; (2) the high number of atoms of isotope leads to different retention time in chromatographic column for samples containing hydrogen and deuterium, hence resulting in assay error; and (3) ICAT can only tag cysteine-containing peptides, hence cannot be used in global analysis of proteins not containing cysteine.

Another type of global labeling reagent can bind with peptides of any form, which comprises the steps of derivatizing the N-terminal amino group or C-terminal acid group and then using mass spectrometry for assay. But the majority of assay reagents being reported in literature have the following drawbacks: (1) the mass spectrometric signals of modified peptides are weakened or prohibited; (2) the incomplete labeling reaction or the exchange between isotopes (hydrogen and deuterium) leads to assay error; and (3) the preparation of assay reagent is tedious and the technique has poor compatibility with other separation techniques (e.g. the different retention time of $^1H$ and $^2D$ labeled peptide fragments in liquid chromatographic column affects the quantitative analysis in mass spectrometry).

The assay of phosphoprotein expression comprises the steps of putting specimen in cell medium containing ($\gamma$-$^{32}P$)-ATP and analyzing the change of phosphorylation from the intensity of $^{32}p$ signals. But this method is time consuming and not entirely safe. A few other technologies that combine stable isotope labeling and mass spectrometry have also been proposed. But their practical applications have room for discussion.

SUMMARY OF THE INVENTION

In addressing the drawbacks of prior art, the present invention aims to provide an accurate, fast and economical platform for the quantification of protein expression, which analyzes the identity and structure of the whole proteome, and at the same time, observes the presence of protein over-expression. This platform would help tremendously the study of pathogenesis and the screening of new drugs.

The object of the present invention is to provide a reagent kit of global analysis for protein expression (GAPE), said reagent kit can label all peptides containing N-terminal amino group or $\epsilon$-amino group of lysine. This global protein analysis reagent kit comprises an aldehyde compound and a reducing agent. The aldehyde compound may be modified with isotopes of different masses.

The isotopes of different masses are hydrogen and deuterium ($^1H$ and $^2D$) or carbon-12 and carbon-13 ($^{12}C$ and $^{13}C$).

The aldehyde compound is formaldehyde, glutaraldehyde, 4(5)-imidazolecarboxaldehyde, or 3-pyrrolidinecarboxaldehyde, preferably formaldehyde.

The reducing agent is sodium cyanoborohydride.

Another object of the present invention is to provide a method for labeling samples using the aforesaid reagent kit for protein expression, comprising the steps of: providing a sample; digesting the sample with enzyme; and adding the global protein analysis reagent kit of the present invention to the sample.

The sample contains one or more kinds of protein; said protein may be chromatographically purified protein; the chromatography technique may be immunochromatography to purify specific protein or strong cation exchange column to achieve fractionation of protein mixture.

The sample may be enzymatically digested and then diluted to the desired concentration and pH with buffer solution; said pH is 5~6; said buffer solution is sodium acetate.

The GAPE reagent kit comprises an aldehyde compound and a reducing agent; and the aldehyde compound may be modified with isotopes of different masses.

The isotopes of different masses are hydrogen and deuterium ($^1H$ and $^2D$) or carbon-12 and carbon-13 ($^{12}C$ and $^{13}C$).

The aldehyde compound is formaldehyde, glutaraldehyde, 4(5)-imidazolecarboxaldehyde, or 3-pyrrolidinecarboxaldehyde, preferably formaldehyde.

The reducing agent is sodium cyanoborohydride.

Yet another object of the present invention is to provide a method for quantifying relative protein expression levels using global analysis reagent kit for protein expression, comprising the steps of: providing two samples to be compared; digesting two samples with enzyme; labeling respectively the digested samples with the reagent kit of global analysis for protein expressionaccording to the present invention; mixing the labeled samples and analyzing said mixed sample using mass spectrometry.

The two samples contain one or more kinds of protein; ant the protein may be chromatographically purified protein. The chromatography technique may be immunochromatography to purify specific protein or strong cation exchange column to achieve fractionation of protein mixture.

After the steps of labeling and mixing the samples, a chromatography step may be added to separate and purify peptides. The chromatography is selected from a group consisting of reverse phase liquid chromatography, strong cation exchange column, and gel column chromatography.

The mass spectrometric analysis of the mixed sample utilizes mass spectrometry coupled with database searching to carry out protein identification and assay of relative protein expression levels.

A further object of the present invention is to provide a method of protein de novo sequencing using a reagent kit of global analysis for protein expression, comprising the steps of: providing a sample; digesting said sample with enzyme; taking a part of digested sample and labeling it with the global analysis reagent kit according to the present invention; mixing the unlabeled sample with the labeled sample; and analyzing the mixture using mass spectrometry.

The sample contains one or more kinds of protein; and the protein may be chromatographically purified protein. The chromatography technique may be immunochromatography to purify specific protein or strong cation exchange column to achieve fractionation of protein mixture.

After the steps of mixing the labeled and unlabeled samples, a chromatography step may be added to separate and purify peptides; The chromatography is selected from a group consisting of reverse phase liquid chromatography, strong cation exchange column, and gel column chromatography.

The mass spectrometric analysis of the sample utilizes signals from tandem mass spectrometry to carry out direct resequencing of amino acids in the peptide fragment.

Yet another object of the present invention is to provide a method for analysis of phosphoprotein using a reagent kit of global analysis for protein expression, comprising the steps of: providing two samples to be compared; digesting the two samples with enzyme; labeling respectively the digested samples with the reagent kit of global analysis for protein expression according to the present invention; mixing the labeled samples; separating and purifying the phosphopeptides using immobilized metal ion affinity chromatography; and analyzing the mixture using mass spectrometry.

The analysis of phosphoprotein means identification of protein or quantitative analysis of relative degree of phosphorylation.

The two samples contain one or more kinds of protein.

The protein may be chromatographically purified protein, and the chromatography technique may be immunochromatography to purify specific protein or strong cation exchange column to achieve fractionation of protein mixture.

DETAILED DESCRIPTION OF THE INVENTION

The object of the present invention is to provide a reagent kit of global analysis for protein expression (i.e. GAPE reagent kit). The GAPE reagent kit comprises an aldehyde compound and a reducing agent. The aldehyde compound may be modified with isotopes of different masses; and the isotopes of different masses may be a couple of hydrogen and deuterium (1H and 2D) or a couple of carbon-12 and carbon-13 (12C and 13C). The aldehyde compound is formaldehyde, glutaraldehyde, 4(5)-imidazolecarboxaldehyde, or 3-pyrrolidinecarboxaldehyde, preferably formaldehyde, and the reducing agent is sodium cyanoborohydride.

The present invention also provides a method for labeling samples using the aforesaid reagent kit of global analysis for protein expression, comprising the steps of: providing a sample; digesting the sample with enzyme; and adding the global protein analysis reagent kit of the present invention to the sample. The steps are further elaborated below: the sample is a protein mixture containing one or more kinds of protein; special proteins in the sample may first be purified using immunochromatography or the protein mixture may be fractionalized using strong cation exchange column; subsequently the protein sample is enzymatically digested into peptide fragments and diluted with sodium acetate solution before the global analysis reagent kit is added. The GAPE reagent kit comprises an aldehyde compound and a reducing agent. The aldehyde compound may be modified with isotopes of different masses, including a couple of hydrogen and deuterium ($^1H$ and $^2D$) or a couple of carbon-12 and carbon-13 ($^{12}C$ and $^{13}C$).

The aldehyde compound, under the aid of reducing agent, would react with the N-terminal amino and ε-amino of lysine in the peptide to form dimethyl amine. The aforesaid reaction is reductive amination, in which the aldehyde compound (formaldehyde or doubly deuterated formaldehyde) reacts with the N-terminal amino and ε-amino of lysine in the peptide, which is then reduced by sodium cyanoborohydride in which primary amine can undergo secondary reductive amination in a short time to be modified into dimethyl amine. This reaction targets the unprotected amino groups of all peptides containing N-terminal amino and lysine. That is, peptides containing multiple lysine are also completely labeled. In the process of ionization during dimethylation, the charge state of peptides is not altered, and the MALDI signals of labeled peptides are oftentimes magnified as compared to unlabeled peptides. Moreover, this reductive amination offers more advantages in reactivity and cost over known technologies. Also the peptides modified with isotopes of different masses can be co-eluted in liquid chromatography (LC), hence making LC more compatible with other separation techniques. It is an improvement of known art.

Figure 1:
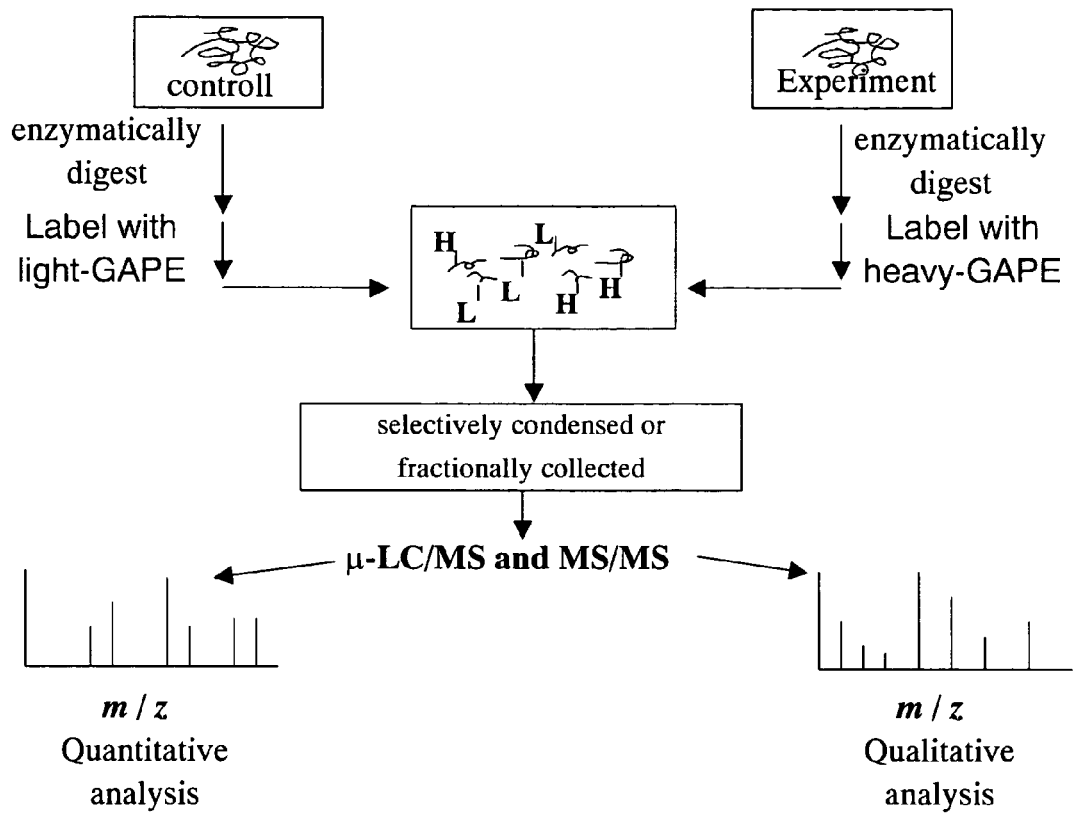
FIG. 1 shows the flow chart for qualitative and quantitative proteomic analysis using the global analysis for protein expression (GAPE) according to the present invention.

By labeling the samples to be compared with aldehyde compound having different isotopes according to the method just described, the corresponding peptides will produce mass difference of 4(1+n), where n is the number of lysine in the peptide. By further combining the labeled peptide sample with another sample according to the purpose of analysis and subjecting the mixture to chromatographic separation and mass spectrometry, the process can detect relative expression levels of proteins, identify protein sequence, and analyze special modifications. FIG. 1 shows the flow chart of proteomic analysis just described.

The present invention is further depicted in the illustration of examples, but the descriptions made in the examples should not be construed as a limitation on the actual application of the present invention.

EXAMPLE 1

The Effect of GAPE Reagent Kit on the Mass Spectrometric Signals of Peptides

Figure 2:
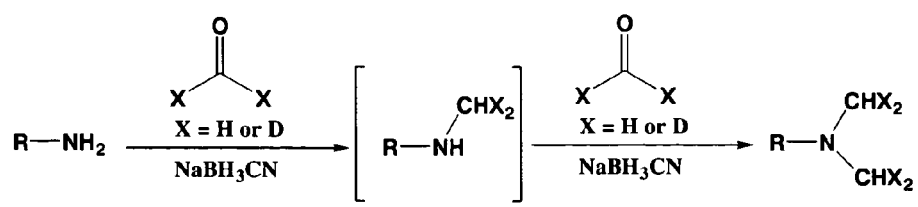
FIG. 2 shows the schematic diagram of reductive amination of peptide.
Figure 3:
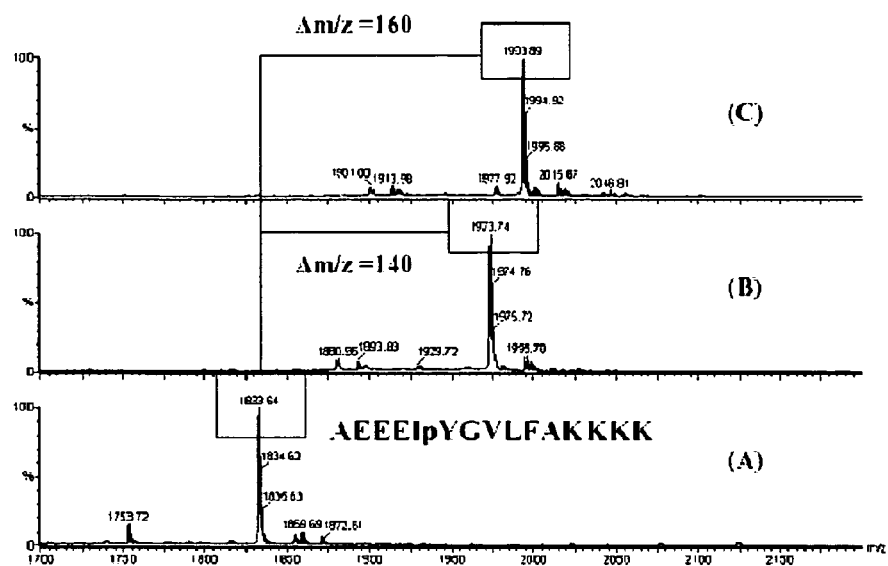
FIG. 3 is the MALDI mass spectrogram of standard phosphopeptide labeled with GAPE according to the present invention, in which (A) is unlabeled; (B) is light-GAPE labeled; and (C) is heavy-GAPE labeled.

Label the standards of phosphopeptides (SEQ: AEEElpYGVLFAKKK) with GAPE reagent kit containing formaldehyde (light-GAPE) and doubly deuterated formaldehyde (heavy-GAPE). The aldehyde compound, under the aid of reducing agent, would react with the N-terminal amino and ε-amino of lysine in the peptide to form dimethyl amine. The reaction takes only 5 minutes and the labeling mechanism is as shown in FIG. 2. Subsequently analyze the labeled samples using MALDI-MS and the results are shown in FIG. 3, in which (A) is the mass spectrogram of phosphopeptide standard not labeled with GAPE reagent kit; (B) is the mass spectrogram of light-GAPE labeled phosphopeptide standard; and (C) is the mass spectrogram of heavy-GAPE labeled phosphopeptide standard. As shown, GAPE reagent kit can specifically label N-terminal amino group and the amino group of lysine in the peptides, and the molecular weight difference between the light-GAPE labeled and heavy-GAPE labeled peptides has the following relationship based on the number of amino group: $\Delta m/z = 4 \times (1+n)$, where n is the number of lysine. The experiment results find that the difference between the molecular weight of unlabeled peptide and light-GAPE labeled peptide is 140 Da, while that between the light-GAPE labeled peptide and heavy-GAPE labeled peptide is 20 Da. The number of lysine in the peptide as derived from the molecular weight difference coincides with the known number of lysine in the peptide sequence of the standard, suggesting the complete reactivity and high specificity of the labeling reaction that is practically free of any by-products.

Figure 4:
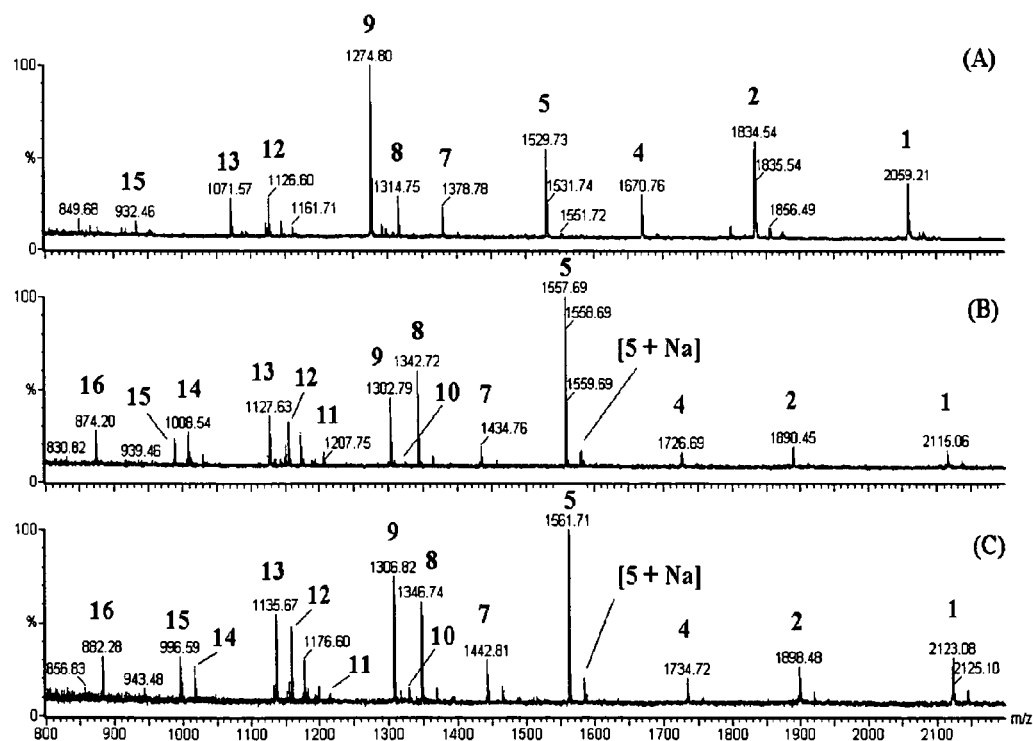
FIG. 4 is the MALDI mass spectrogram of hemoglobin digest labeled with the GAPE according to the present invention, in which (A) is unlabeled; (B) is light-GAPE labeled; and (C) is heavy-GAPE labeled.

Next, take hemoglobin digest sample and label it with the GAPE reagent kit. The results are as shown in FIG. 4, in which (A) is the MALDI mass spectrogram of unlabeled hemoglobin digest; (B) is the MALDI mass spectrogram of light-GAPE labeled hemoglobin digest; (C) is MALDI mass spectrogram of heavy-GAPE labeled hemoglobin digest. As shown, the difference between the molecular weight of peptides marked by a number in (A) and that of peptides marked by the same number in (B) and (C) is the integer multiple of the molecular weight increase of light-GAPE labeled hemoglobin digest (28 Da) and the molecular weight increase of heavy-GAPE labeled hemoglobin digest (32 Da), indicating the complete reaction and high specificity of the GAPE reagent kit.

Figure 5:
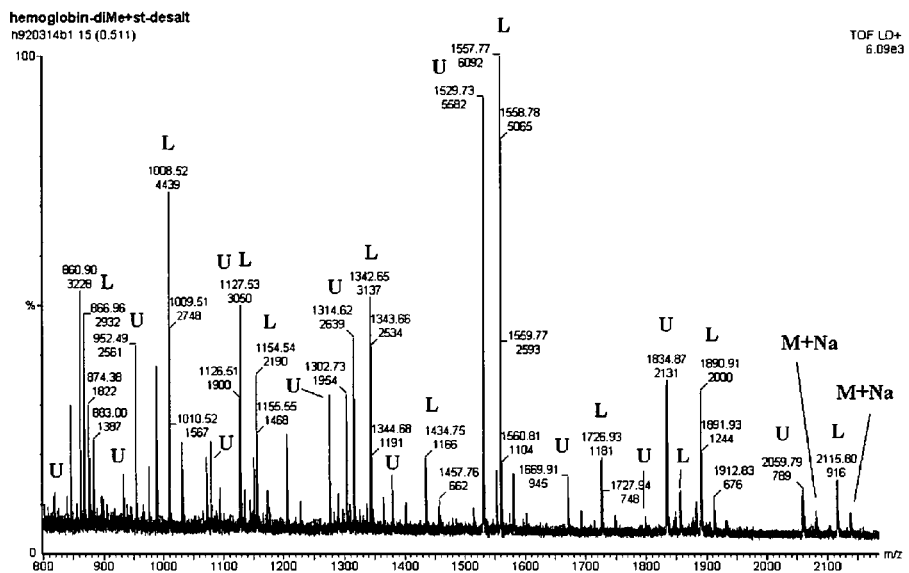
FIG. 5 depicts the mass spectrometry signals of an equivalent mixture of light-GAPE labeled and unlabeled hemoglobin digests.

FIG. 5 is the MALDI mass spectrogram of equivalent mixture of light-GAPE labeled and unlabeled samples. The difference between the molecular weight of dimethylated peptides derived from light-GAPE labeling and unlabeled peptides is (n×28)+28. A comparison of their mass spectrometric signals also shows that the signal intensity of dimethylated peptides is in general higher than that of unlabeled peptides.

EXAMPLE 2

The Effect of GAPE Reagent Kit on Retention Time in Liquid Chromatography

Figure 6:
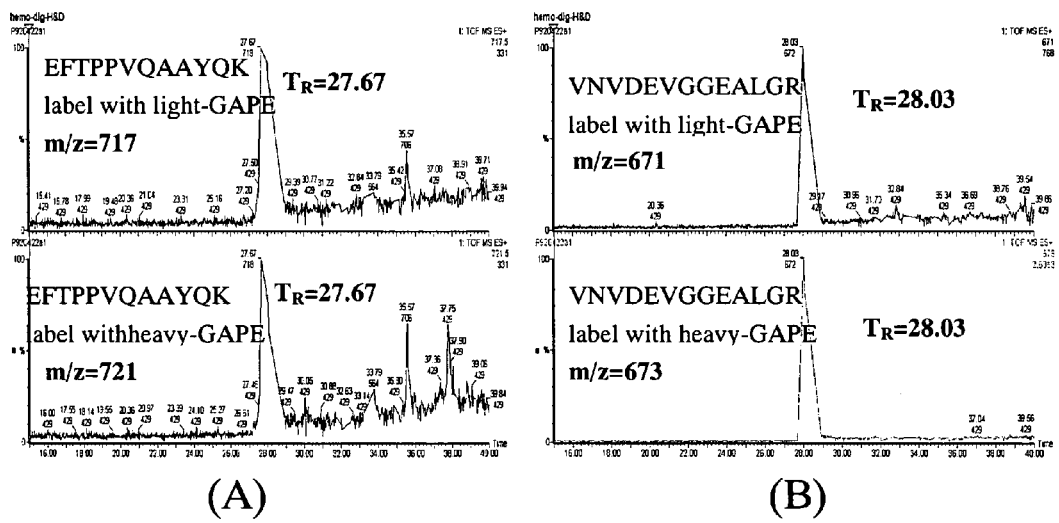
FIG. 6 depicts the retention time of light-GAPE labeled peptide and heavy-GAPE labeled peptide.

Provide two equivalent hemoglobin digest samples and label them with light-GAPE and heavy-GAPE respectively. Mixed the two labeled samples and analyze with liquid chromatography-mass spectrometry (LC-MS). The results are shown in FIG. 6. FIG. 6(A) shows the retention time of peptides (SEQ:EFTPPVQAAYQK), which is 27.67 minutes for both light-GAPE and heavy-GAPE modified peptides; FIG. 6(B) shows the retention time of peptides (SEQ: VNVDEVGGEALGR), which is 28.03 minutes for both light-GAPE and heavy-GAPE modified peptides. In summary of the results in FIG. 6, the light-GAPE and heavy-GAPE modified peptides have the same retention time in LC, which provides an ideal condition for subsequent MC analyses.

EXAMPLE 3

Detection of Relative Protein Expression Levels Using GAPE Reagent Kit

Figure 7:
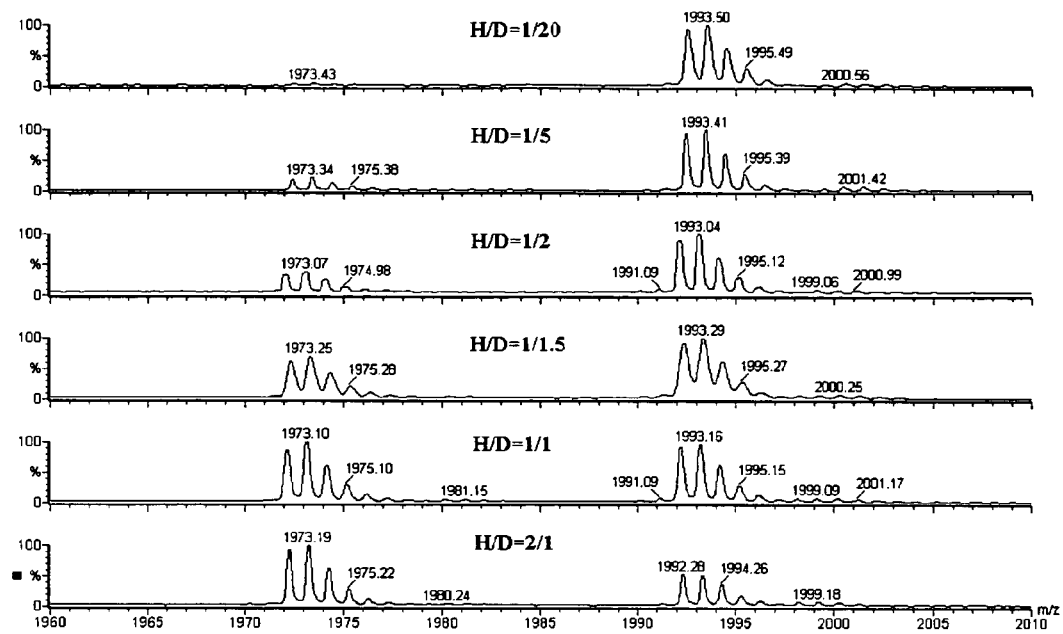
FIG. 7 depicts the mass spectrometry signals of mixtures of light-GAPE and heavy-GAPE labeled standard phosphopeptides mixed in different ratios.
Figure 8:
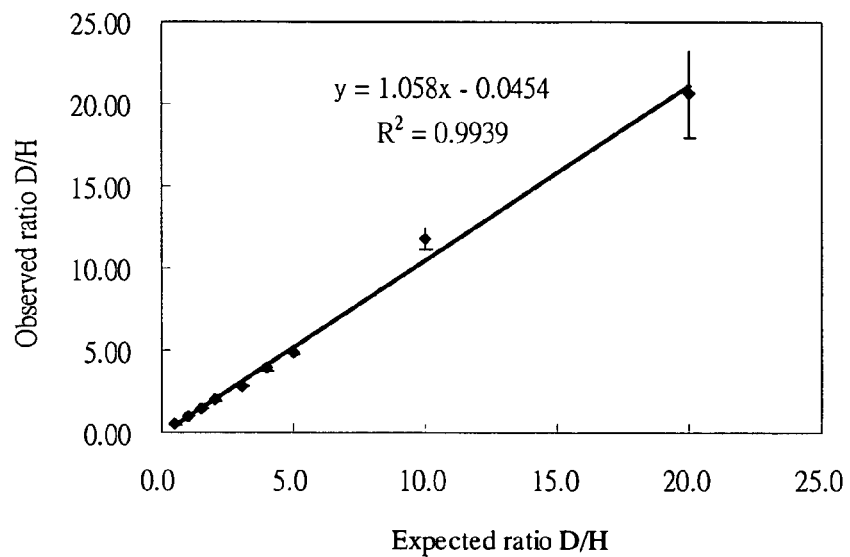
FIG. 8 shows the linear graph of mix ratio vs. relative intensity of MS signals obtained from FIG. 6.

Label phosphopeptide standards (SEQ:AEEElpYGVL-FAKKK) with light-GAPE and heavy-GAPE, and then mix the labeled samples in different ratios (2:1, 1:1, 1:1.5, 1:2, 1:5, 1:20). Analyze the mixed samples using MALDI-MS. Based on the results as shown in FIG. 7, the molecular weight difference between light-GAPE and heavy-GAPE modified peptides in mass spectrometry is 4(n+1) and the relative intensity of MS signals are consistent with the mix ratio. FIG. 8 is the result of mix ratio plotted against relative intensity of MS signals, which shows excellent linear relationship ($R^2=0.9939$), indicating that the GAPE reagent kit can accurately detect the relative protein expression levels.

EXAMPLE 4

Using GAPE Reagent Kit for Protein De Novo Sequencing

Provide two hemoglobin digest samples in proper amount. Label one of the samples with GAPE reagent kit and then mix it with the unlabeled sample. Use tandem mass spectrometry (MS-MS) for analysis. In the MS-MS, peptides were fractioned into sets of b ions and y ions. The amino acids in the peptide fragment can be de novo sequenced by comparing the difference between the adjacent b-ions or y-ions with the molecular weight of amino acids and the results are depicted in Table 1. As shown, GAPE labeled peptides have more intact b-ion series and y-ion series, and hence are more suitable for protein de novo sequencing.

TABLE 1

Collision induced dissociation (CID) of GAPE labeled and unlabeled peptides

| # | Unlabeled b-ion (theoretical value) | Unlabeled b-ion (observed) | Labeled b-ion (theoretical value) | Labeled b-ion (observed) | Sequence | Unlabeled y-ion (theoretical value) | Unlabeled y-ion (observed) | Labeled y-ion (theoretical value) | Labeled y-ion (observed) | # |
|---|---|---|---|---|---|---|---|---|---|---|
| 1 | 100.8 | | 128.11 | | V | | | | | 13 |
| 2 | 214.12 | 214.12 | 242.15 | 242.15 | N | 1215.60 | 1215.60 | 1215.60 | 1215.60 | 12 |
| 3 | 313.19 | 313.19 | 341.22 | 341.22 | V | 1101.55 | 1101.55 | 1101.55 | 1101.55 | 11 |
| 4 | 428.21 | | 456.25 | 456.25 | D | 1002.49 | 1002.49 | 1002.49 | 1002.49 | 10 |
| 5 | 557.26 | | 585.29 | 585.29 | E | 887.46 | | 887.46 | 887.46 | 9 |
| 6 | 656.33 | | 684.36 | 684.36 | V | 758.42 | 758.42 | 758.42 | 758.42 | 8 |
| 7 | 713.35 | | 741.38 | 741.38 | G | 659.35 | | 659.35 | 659.35 | 7 |
| 8 | 770.37 | | 798.40 | | G | 602.33 | 602.33 | 602.33 | 602.33 | 6 |
| 9 | 899.41 | | 927.44 | 927.44 | E | 545.30 | | 545.30 | 545.30 | 5 |
| 10 | 970.45 | | 998.48 | 998.48 | A | 416.26 | 416.26 | 416.26 | 416.26 | 4 |
| 11 | 1083.53 | | 1111.56 | | L | 345.23 | 345.23 | 345.23 | 345.23 | 3 |
| 12 | 1140.55 | | 1168.58 | | G | 232.14 | 232.14 | 232.14 | | 2 |
| 13 | | | | | R | 175.12 | | 175.12 | 175.12 | 1 |

※ Peptide sequence: VNVDEVGGEALGR
※ The unbolded letters depict predicted CID and bolded letters are detected CID.

EXAMPLE 5

Quantitative Analysis of Protein Mixture Using GAPE Reagent Kit

Figure 9:
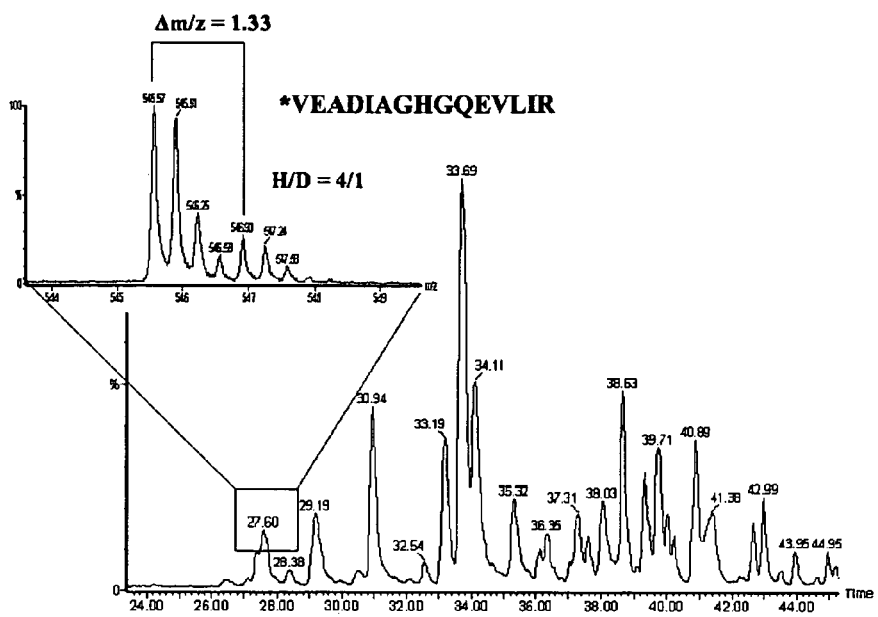
FIG. 9 shows the mass spectrogram of peptide in triplet state and isotopically labeled at one end.

Mix ovalbumin, bovine serum albumin and myoglobin in the ratio of 2:2:4 and 5:2:1. Simulate control group and test group by labeling the mixtures with light-GAPE and heavy-GAPE respectively. The results of LC-MS analysis as depicted in Table 2 show acceptable accuracy and precision. Also as shown in FIG. 9, the difference between the mass-to-charge ratio of light-GAPE labeled peptides and heavy-GAPE labeled peptides is still measurable in mass spectrometry even in triplet state (trivalent charge state).

TABLE 2

GAPE analysis of mixtures of three proteins in two different ratios to simulate real samples

| Protein | Identified peptide sequence | Valence | Number of label | Observed ratio | Expected ratio | Ave. SD | Error (%) |
|---|---|---|---|---|---|---|---|
| Ovalbumin | ADHPFLFCIK | 3 | 2 | 2.20 | 2.50 | 2.50 ± 0.29 | 0 |
|  | AFKDEDTQAMPFR | 3 | 2 | 2.24 | 2.50 |  |  |
|  | HIATNAVLFFGR | 2 | 1 | 2.63 | 2.50 |  |  |
|  | DILNQITKPNKVYSFSLASR | 3 | 2 | 2.84 | 2.50 |  |  |
|  |  | 2 | 2 | 2.54 | 2.50 |  |  |
|  | YPILPEYLQCVK | 2 | 2 | 2.01 | 2.50 |  |  |
|  | LTEWTSSNVMEER | 2 | 1 | 2.70 | 2.50 |  |  |
|  | GGLEPINFQTAADQAR | 2 | 1 | 2.47 | 2.50 |  |  |
|  | ELINSWVESQTNGIIR | 2 | 1 | 2.84 | 2.50 |  |  |
| Bovine serum albumin | SLHTLFGDELCK | 3 | 2 | 0.93 | 1.00 | 0.97 ± 0.07 | 3 |
|  |  | 2 | 2 | 0.91 | 1.00 |  |  |
|  | QTALVELLK | 2 | 2 | 0.91 | 1.00 |  |  |
|  | KVPQVSTPTLVEVSR | 3 | 2 | 0.94 | 1.00 |  |  |
|  | LKPOPNTLCDEFK | 3 | 3 | 0.95 | 1.00 |  |  |
|  | LVNELTEFAK | 2 | 2 | 0.90 | 1.00 |  |  |
|  | HLVDEPQNLIK | 2 | 2 | 0.90 | 1.00 |  |  |
|  | TVMENFVAFVDK | 2 | 2 | 1.12 | 1.00 |  |  |
|  | EYEATLEECCAK | 2 | 2 | 1.00 | 1.00 |  |  |
|  | DAFLGSFLYEYSR | 2 | 1 | 1.08 | 1.00 |  |  |
|  | LFTFHADICTLPDTEK | 3 | 2 | 1.03 | 1.00 |  |  |
| Myoglobin | HGTVVLTALGGILK | 2 | 2 | 0.21 | 0.25 | 2.24 ± 0.03 | 4 |
|  | VEADIAGHGQEVLIR | 2 | 1 | 0.25 | 0.25 |  |  |
|  |  | 3 | 1 | 0.27 | 0.25 |  |  |
|  | GLSDGEWQQVLNVWGK | 2 | 2 | 0.19 | 0.25 |  |  |
|  | YLEFISDAIIHVLHSK | 3 | 2 | 0.28 | 0.25 |  |  |

EXAMPLE 6

Detection of Protein Phosphorylation Using GAPE Reagent Kit

Figure 10:
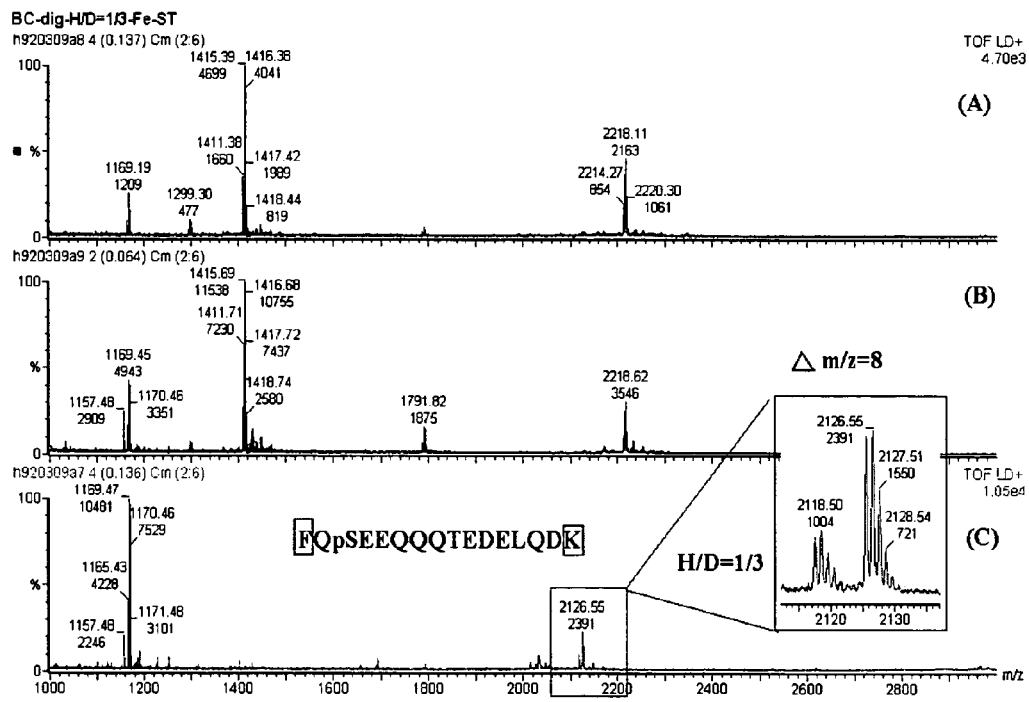
FIG. 10 is the MALDI mass spectrogram of phosphoprotein using GAPE and IMAC to analyze phosphorylation of protein, in which (A) shows the phosphoprotein before purification; (B) shows IMAC-removed non-phosphopeptides; and (C) shows IMAC-condensed phosphopeptides.

Provide two β-casein digest samples of proper amount and mix by the ratio of 1:3 after labeling them with light-GAPE and heavy-GAPE respectively to simulate the different degrees of phosphorylation of proteins. Purify the phosphopeptides in the mixture using immobilized metal ion affinity chromatography (IMAC). Use mass spectrometry to analyze the non-purified and purified samples. The results are as shown in FIG. 10, in which (A) is phosphopeptides that did not go through IMAC purification and undetected by MS; (B) is the signals of non-phosphopeptides removed by IMAC, and (C) is the signals of IMAC-purified phosphopeptides. To sum up, the GAPE reagent kit combined with IMAC can detect phosphopeptides and analyze the relative expression levels of phosphopeptides.

The GAPE reagent kit disclosed in the present invention offer the following advantages: (1) it can label all types of peptides; (2) the price of its labeling reagent is relatively cheap; (3) the reaction of labeling reagent is fast and complete; (4) the signals of labeled peptides are enhanced in mass spectrometry; (5) peptides modified with formaldehyde and doubly deuterated formaldehyde have excellent co-elution effect in liquid chromatography; (6) it is highly compatible with other separation techniques; (7) it can work in conjunction with IMAC in the quantitative analysis of protein phosphorylation. This invention in combination with chromatography (strong cation exchange column, reverse phase liquid chromatography, IMAC, or immunochromatography) and mass spectrometry provide a power research tool in the study of pathogenesis, and with the addition of disease marker, screening of drugs based on the over-expression of protein.

All modifications and alterations made by those familiar with the skill without departing from the spirits of the invention and appended claims shall remain within the protected scope and claims of the invention.

What is claimed is:

1. A reagent kit of global analysis for protein expression, comprising:
   a $^1$H-labeled formaldehyde;
   a $^2$D-labeled formaldehyde; and
   a reducing agent which is sodium cyanoborohydride.

* * * * *